(12) United States Patent
Kovach

(10) Patent No.: US 9,125,653 B2
(45) Date of Patent: Sep. 8, 2015

(54) FLEXIBLE NOSECONE FOR PERCUTANEOUS DEVICE

(71) Applicant: St. Jude Medical, Cardiology Division, Inc., St. Paul, MN (US)

(72) Inventor: Melinda K. Kovach, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 228 days.

(21) Appl. No.: 13/781,992

(22) Filed: Mar. 1, 2013

(65) Prior Publication Data

US 2014/0039531 A1 Feb. 6, 2014

Related U.S. Application Data

(60) Provisional application No. 61/678,854, filed on Aug. 2, 2012.

(51) Int. Cl.
*A61B 17/08* (2006.01)
*A61B 17/10* (2006.01)
(Continued)

(52) U.S. Cl.
CPC .......... *A61B 17/083* (2013.01); *A61B 17/00234* (2013.01); *A61B 17/068* (2013.01);
(Continued)

(58) Field of Classification Search
CPC ................ A61B 17/00234; A61B 17/00243; A61B 17/08; A61B 17/083; A61B 17/122; A61B 17/1227; A61B 17/10; A61B 17/068; A61B 17/128; A61B 17/1285; A61B 2019/082; A61B 2019/083; A61B 2019/4805; A61B 2019/481; A61F 2/2463
USPC .......... 600/101, 104, 105, 106; 606/108, 127, 606/128, 139, 142, 143, 151, 157, 158, 191, 606/192, 193, 194, 195, 196, 197, 198, 199, 606/200; 623/1.11, 1.12, 1.23
See application file for complete search history.

(56) References Cited

U.S. PATENT DOCUMENTS 5,156,608 A 10/1992 Troidl et al.
5,601,573 A 2/1997 Fogelberg et al.
(Continued)

FOREIGN PATENT DOCUMENTS

AU 2002300522 B2 1/2007
WO 9620749 A1 7/1996
(Continued)

OTHER PUBLICATIONS

Merriam-Webster definition of "fabric" as accessed on Dec. 17, 2014; http://www.merriam-webster.com/dictionary/fabric.*
(Continued)

*Primary Examiner* — Jonathan W Miles
(74) *Attorney, Agent, or Firm* — Lerner, David, Littenberg, Krumholz & Mentlik, LLP

(57) ABSTRACT

A for gathering tissue of a heart valve leaflet may include an outer tube extending in an elongation direction and having an open distal end, a capture tool movable in the outer tube between a contained position and a use position, a tissue securing component disposed at the open distal end of the outer tube, a nosecone removably assembled over the open distal end of the outer tube in a protective condition, and an actuation member joined to a central portion of the nosecone and extending into a lumen of the outer tube. The capture tool may be operable to capture tissue of the heart valve leaflet. The nosecone may have a central portion that extends across the open distal end of the outer tube and a peripheral portion surrounding the central portion and overlying an outer surface of the outer tube adjacent the open distal end.

17 Claims, 2 Drawing Sheets

(51) Int. Cl.
*A61B 17/128* (2006.01)
*A61B 17/00* (2006.01)
*A61B 17/068* (2006.01)
A61B 17/04 (2006.01)
A61B 17/122 (2006.01)
A61B 17/064 (2006.01)
A61B 19/08 (2006.01)
A61B 19/00 (2006.01)
A61F 2/24 (2006.01)

(52) U.S. Cl.
CPC ............... *A61B 17/10* (2013.01); *A61B 17/128* (2013.01); *A61B 17/0467* (2013.01); *A61B 17/1227* (2013.01); *A61B 17/1285* (2013.01); *A61B 2017/00243* (2013.01); *A61B 2017/00349* (2013.01); *A61B 2017/00783* (2013.01); *A61B 2017/0417* (2013.01); *A61B 2017/0464* (2013.01); *A61B 2017/0645* (2013.01); *A61B 2019/083* (2013.01); *A61B 2019/307* (2013.01); *A61B 2019/481* (2013.01); *A61F 2/2463* (2013.01)

(56) References Cited

U.S. PATENT DOCUMENTS

| | | | |
|---|---|---|---|
| 5,749,879 | A | 5/1998 | Middleman et al. |
| 5,921,993 | A | 7/1999 | Yoon |
| 6,440,152 | B1 | 8/2002 | Gainor et al. |
| 6,569,182 | B1* | 5/2003 | Balceta et al. ............... 606/200 |
| 6,752,813 | B2 | 6/2004 | Goldfarb et al. |
| 6,945,978 | B1 | 9/2005 | Hyde |
| 7,011,669 | B2 | 3/2006 | Kimblad |
| 7,464,712 | B2 | 12/2008 | Oz et al. |
| 7,569,062 | B1 | 8/2009 | Kuehn et al. |
| 7,758,595 | B2 | 7/2010 | Allen et al. |
| 8,777,966 | B2 | 7/2014 | Dale et al. |
| 2001/0016750 | A1 | 8/2001 | Malecki et al. |
| 2002/0013571 | A1 | 1/2002 | Goldfarb et al. |
| 2002/0107531 | A1 | 8/2002 | Schreck et al. |
| 2003/0093071 | A1 | 5/2003 | Hauck et al. |
| 2004/0039442 | A1 | 2/2004 | St. Goar et al. |
| 2004/0181238 | A1 | 9/2004 | Zarbatany et al. |
| 2004/0193185 | A1 | 9/2004 | McBrayer |
| 2005/0090837 | A1 | 4/2005 | Sixto et al. |
| 2005/0096671 | A1 | 5/2005 | Wellman et al. |
| 2005/0107871 | A1 | 5/2005 | Realyvasquez et al. |
| 2005/0125011 | A1 | 6/2005 | Spence et al. |
| 2005/0143763 | A1 | 6/2005 | Ortiz et al. |
| 2005/0149072 | A1 | 7/2005 | DeVries et al. |
| 2005/0177176 | A1 | 8/2005 | Gerbi et al. |
| 2005/0251161 | A1 | 11/2005 | Saadat et al. |
| 2006/0122633 | A1 | 6/2006 | To et al. |
| 2006/0173422 | A1* | 8/2006 | Reydel et al. ............... 604/271 |
| 2007/0049952 | A1 | 3/2007 | Weiss |
| 2007/0102474 | A1 | 5/2007 | Shelton et al. |
| 2007/0102475 | A1 | 5/2007 | Ortiz et al. |
| 2007/0142846 | A1 | 6/2007 | Catanese et al. |
| 2007/0162056 | A1 | 7/2007 | Gerbi et al. |
| 2007/0197858 | A1 | 8/2007 | Goldfarb et al. |
| 2007/0225734 | A1 | 9/2007 | Bell et al. |
| 2008/0294175 | A1 | 11/2008 | Bardsley et al. |
| 2008/0300624 | A1 | 12/2008 | Schwemberger et al. |
| 2009/0062852 | A1 | 3/2009 | Marino |
| 2009/0118744 | A1 | 5/2009 | Wells et al. |
| 2009/0125038 | A1 | 5/2009 | Ewers et al. |
| 2009/0149870 | A1* | 6/2009 | Jugenheimer et al. ........ 606/142 |
| 2011/0054521 | A1 | 3/2011 | Ventura et al. |
| 2011/0077668 | A1 | 3/2011 | Gordon et al. |
| 2011/0087242 | A1 | 4/2011 | Pribanic et al. |
| 2011/0114700 | A1 | 5/2011 | Baxter, III et al. |
| 2011/0230897 | A1 | 9/2011 | Palermo et al. |
| 2011/0313432 | A1 | 12/2011 | Miles et al. |
| 2012/0226291 | A1 | 9/2012 | Malizia et al. |
| 2013/0046332 | A1* | 2/2013 | Jones et al. ............... 606/200 |
| 2014/0039607 | A1 | 2/2014 | Kovach |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 0200121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report and Written Opinion for Application No. PCT/US2013/065360 dated Apr. 23, 2014.
International Search Report for Application No. PCT/US2012/023437 dated Apr. 24, 2012.
International Search Report for Application No. PCT/US2013/052832 dated Jan. 15, 2014.
International Search Report and Written Opinion for Application No. PCT/US2013/052843 dated Oct. 11, 2013.
International Search Report and Written Opinion for Application No. PCT/US2013/052838 dated Oct. 11, 2013.
International Search Report and Written Opinion for Application No. PCT/US2013/052822 dated Jan. 21, 2014.
International Preliminary Report on Patentability for Application No. PCT/US2012/023437 dated Aug. 6, 2013.
International Search Report for Application No. PCT/US2013/023077 dated May 14, 2013.
International Search Report and Written Opinion for Application No. PCT/US2013/023082 dated Oct. 1, 2013.
International Search Report and Written Opinion for Application No. PCT/US2013/024304 dated Jul. 5, 2013.

* cited by examiner

FLEXIBLE NOSECONE FOR PERCUTANEOUS DEVICE

CROSS-REFERENCE TO RELATED APPLICATION

The present application claims the benefit of the filing date of U.S. Provisional Patent Application No. 61/678,854 filed Aug. 2, 2012, the disclosure of which is hereby incorporated herein by reference.

BACKGROUND OF THE INVENTION

The present invention is related to percutaneous tissue access, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be broken. As a result, the valve does not close normally, and the unsupported valve leaflet may bulge back, or "prolapse," into the left atrium like a parachute. Thus, as the ventricle contracts, the abnormal leaflet may be propelled backwards, beyond its normal closure line into the left atrium, thereby allowing blood to flow back into the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

Percutaneous devices and methods for gathering tissue of a heart valve leaflet are disclosed. A device for gathering tissue of a heart valve leaflet may include an outer tube extending in an elongation direction and having an open distal end, a capture tool movable in the outer tube between a contained position and a use position, a tissue securing component disposed at the open distal end of the outer tube, a nosecone removably assembled over the open distal end of the outer tube in a protective condition, and an actuation member joined to a central portion of the nosecone and extending into a lumen of the outer tube. The outer tube may have an outer surface and the lumen extending therethrough. The capture tool may be operable to capture tissue of the heart valve leaflet and to draw the captured tissue into the outer tube in a gathered configuration. The tissue securing component may be adapted to be applied to the captured tissue to hold the captured tissue in the gathered configuration. The nosecone may have the central portion that extends across the open distal end of the outer tube and a peripheral portion surrounding the central portion and overlying the outer surface of the outer tube adjacent the open distal end.

The actuation member may be non-rigid. The actuation member may be rigid. The actuation member may be joined to the nosecone substantially at the center of the central portion. The nosecone may be configured to change shape from the protective condition to an inverted condition when the actuation member is pulled in the elongation direction. The nosecone may be made of a fabric. The nosecone may be made of silicone. The nosecone may be configured to move from the protective condition to a collapsed condition when the actuation member is removed from the outer tube. The nosecone may be made of a shape memory material.

The nosecone may include a slit extending from a free edge of the nosecone toward the central portion of the nosecone. The slit may divide the peripheral portion into a plurality of sections such that when the actuation member is pulled in the elongation direction, the plurality of sections separate from one another. The nosecone may include a line of perforations extending from a free edge of the nosecone toward the central portion of the nosecone. The line of perforations may divide the peripheral portion into a plurality of sections such that when the actuation member is pulled in the elongation direction, the perforations tear to separate the sections from one another.

The tissue securing component may be a clip. The clip may be assembled in an expanded condition around the outer tube and may be biased to contract to a clamping condition when deployed from the outer tube. The device may also include a deployment tube slidably disposed around the outer tube. The deployment tube may be movable between a proximal position in which an end surface thereof is spaced apart from the open distal end of the outer tube and a distal position in which the end surface is adjacent the open distal end. The end surface of the deployment tube may be adapted to push the clip off of the outer tube when the deployment tube is moved from the proximal position to the distal position.

A transcatheter method of gathering tissue of a heart valve leaflet may include inserting an elongated catheter assembly to a position adjacent the heart valve leaflet. The catheter assembly may include an outer tube extending in an elongation direction, a capture tool movable in the outer tube between a contained position and a use position, and a nosecone movable between a protective condition enclosing an open distal end of the outer tube and a deployed condition removed from the distal end of the outer tube. The method may also include moving the nosecone from the protective condition to the deployed condition to thereby expose the open distal end of the outer tube, moving the capture tool from the contained position to the use position, capturing tissue of the heart valve leaflet with the capture tool, retracting the capture tool from the use position toward the contained position to draw the captured tissue into the outer tube in a gathered configuration, and securing the captured tissue substantially in the gathered configuration.

The elongated catheter assembly may include an actuation member joined to a central portion of the nosecone. The step of moving the nosecone may include pulling the actuation member in the elongation direction until the nosecone is pulled into a lumen of the outer tube. The actuation member may be non-rigid. The step of moving the nosecone may include pushing the actuation member in the elongation direction until the nosecone is pushed off of the distal end of the outer tube. The step of moving the nosecone may also include pulling the actuation member in the elongation direction until the nosecone is pulled into a lumen of the outer tube. The outer tube may have a lumen with a predetermined cross-section, and the nosecone may be made of a shape memory material and may be biased toward a collapsed shape, the collapsed shape having a cross-section that is smaller than the predetermined cross-section. The nosecone may take the collapsed shape after being pushed off of the distal end of the outer tube. The actuation member may be rigid.

The nosecone may have a central portion, a peripheral portion surrounding the central portion, and a slit extending from a free edge of the nosecone toward the central portion of the nosecone and dividing the peripheral portion into a plurality of sections. The step of moving the nosecone may include separating the plurality of sections from one another. The nosecone may have a central portion, a peripheral portion surrounding the central portion, and a line of perforations extending from a free edge of the nosecone toward the central portion of the nosecone and dividing the peripheral portion into a plurality of sections. The step of moving the nosecone may include separating the plurality of sections from one another along the line of perforations.

The tissue securing component may be a clip assembled in an expanded condition around the outer tube and biased to contact to a clamping condition. The securing step may include deploying the clip from the outer tube, whereupon the clip contracts to the clamping condition around the captured tissue. The catheter assembly may also include a deployment tube slidably disposed around the outer tube. The securing step may include moving the deployment tube from a proximal position in which an end surface thereof is spaced apart from the open distal end of the outer tube to a distal position in which the end surface is adjacent the open distal end, such that the deployment tube pushes the clip off of the outer tube.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
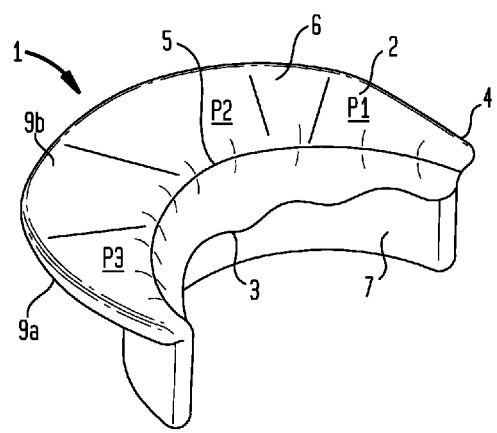
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 also has a lower surface 9a and an upper surface 9b. The posterior leaflet 2 has three scalloped portions P1, P2, and P3, any of which may include a portion that is billowed, loose, or floppy, and which therefore may be the cause of a prolapse condition of the valve. The inventive devices, systems, and methods described herein may be adapted to repair such a billowed, loose, or floppy portion of the posterior leaflet 2 or the anterior leaflet 3.

Figure 2:
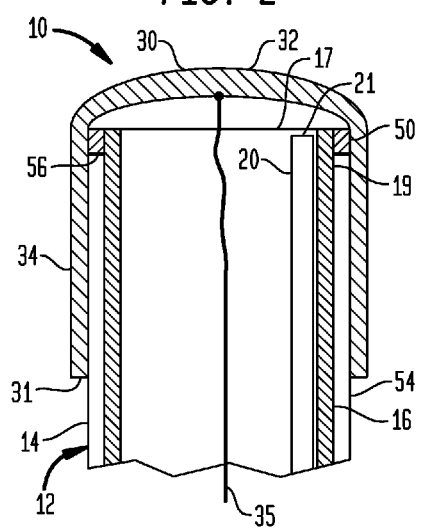
FIG. 2 is a diagrammatic longitudinal cross-sectional view of the flexible nosecone and distal end of a device for transcatheter gathering of heart valve leaflet tissue, shown with the nosecone in an initial condition.
Figure 3:
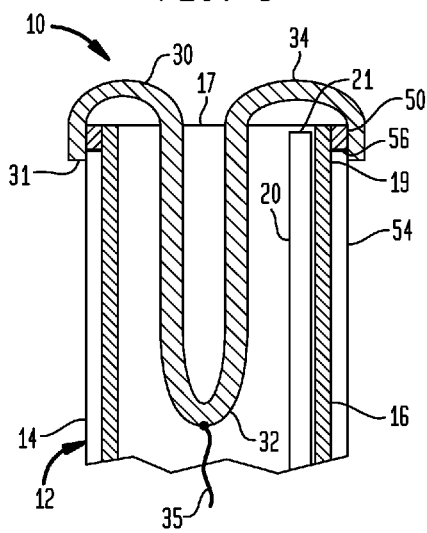
FIG. 3 is a diagrammatic longitudinal cross-sectional view of the flexible nosecone and distal end of the device of FIG. 2, shown with the nosecone in a partially retracted condition.

Referring to FIGS. 2 and 3, an exemplary device 10 for percutaneous access to tissue in a patient, such as for gathering of heart valve leaflet tissue, includes an elongated catheter assembly 12 adapted to be inserted through the apex of a human heart so that a distal portion 14 of the catheter assembly may reach the patient's mitral valve 1 for repair thereof.

The catheter assembly 12 includes a containment tube 20 longitudinally slideable within an outer tube 16 between a retracted position within the lumen of the outer tube (FIGS. 2 and 3) and a deployed position (FIG. 5) in which a distal end 21 of the containment tube protrudes distally beyond the open distal end 17 of the outer tube. The outer tube 16 may be made of one or more echogenic materials, so that the outer tube may be more easily visualized inside a patient using three-dimensional echocardiography.

A nosecone 30 may be removably assembled over the open distal end 17 of the outer tube 16. The nosecone 30 may serve to minimize traumatic injury to the heart or blood vessels resulting from contact with the open distal end 17 of the outer tube 16 during insertion of the device 10 into a patient, for example, through the apex of the heart into the left ventricle. The nosecone 30 may be made of a fabric or another flexible material (e.g., silicone) that is capable of changing shape from a protective condition (FIG. 2) to an inverted or deployed condition (FIG. 3). The material of the nosecone 30 may be permeable or non-permeable with respect to penetration by liquids.

The nosecone 30 may have a central portion 32 that is configured to extend across the open distal end 17 of the outer tube 16 when the nosecone is in the protective condition. A peripheral portion 34 of the nosecone 30 surrounding the central portion 32 may be configured to overlie the outer surface 19 of the outer tube 16 adjacent the open distal end 17 thereof when the nosecone is in the protective condition.

An actuation member 35 may be joined substantially to the center of the nosecone 30. A free end of the actuation member 35 may extend proximally through the outer tube 16 to a proximal portion of the device 10 (not shown), where it may be grasped by the user or connected to an actuation mechanism operable by the user. The actuation member 35 may be, for example, a non-rigid suture or wire, or it may be a rigid shaft, tube, or wire.

Figure 4:
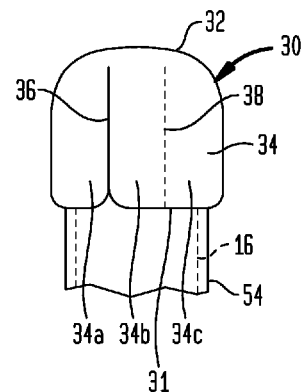
FIG. 4 is a diagrammatic side view of the flexible nosecone and the distal end of the device of FIG. 2.

As shown in FIG. 4, the peripheral portion 34 of the nosecone 30 may include one or more preformed slits 36 or tearable perforations 38 extending from the free edge 31 of the nosecone toward the central portion 32 thereof. When the free end of the suture 35 is pulled by a user as described below, these slits 36 or perforations 38 cause the peripheral portion 34 of the nosecone 30 to separate into sections, such as sections 34a, 34b, and 34c, thereby reducing the resistance to the movement of the nosecone to the inverted condition.

Figure 5:
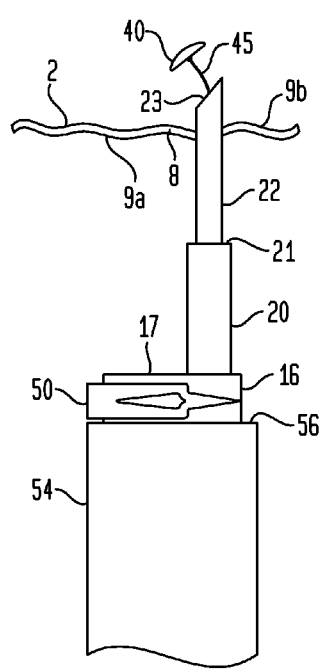
FIG. 5 is a diagrammatic side view of the distal end of the device of FIG. 2, showing the tissue capture tool engaged with the posterior leaflet of the mitral valve of FIG. 1.
Figure 6:
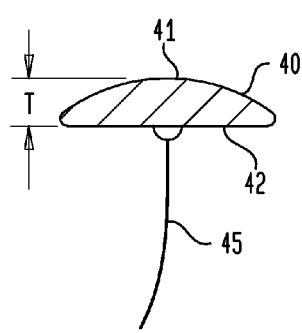
FIG. 6 is an enlarged diagrammatic side view of the distal portion of the tissue capture tool of FIG. 5.
Figure 7:
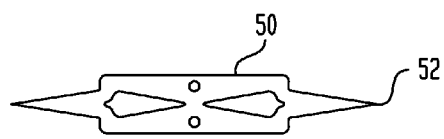
FIG. 7 is a plan view of a clip for use with the device of FIG. 2, shown in a flat condition.

Referring to FIGS. 5 and 6, the device 10 may include a tissue capture tool in the form of a needle 22 and a resorbable anchor 40. The needle 22 may be longitudinally slideable within the containment tube 20 between a retracted or contained position substantially entirely within the lumen of the containment tube (FIGS. 2 and 3), and a deployed or use position in which a tapered distal end 23 of the needle protrudes from the distal end 21 of the containment tube (FIG. 5).

The resorbable anchor 40 may initially be stored within the needle 22 and may be deployable therefrom for use. The anchor 40 may have a maximum thickness T between its top surface 41 and bottom surface 42 that is equal to or slightly smaller than the diameter of the lumen of the needle 22. The anchor 40 may be deployed from the needle 22 by increasing the pressure within the needle, using pressurized saline, for example, so that an expelling force applied to the anchor is greater than the frictional forces holding the anchor in place.

An anchor retention member 45 in the form of a wire or suture may be joined substantially to the center of the bottom surface 42 of the anchor 40, such that the anchor can pivot with respect to the retention member. A free end of the retention member 45 may extend proximally through the needle 22, the containment tube 20, and the outer tube 16 to a proximal portion of the device 10 (not shown), where it may be grasped by the user or connected to an actuation mechanism operable by the user.

The device 10 may optionally include a cutting tube (not shown) for detaching the retention member 45 from the resorbable anchor 40. The cutting tube may be telescopically mounted within the containment tube 20 and around the needle 22 for sliding movement between a retracted position substantially entirely within the lumen of the containment tube, and a deployed position in which a sharpened distal end of the cutting tube protrudes from the distal end 21 of the containment tube. The sharp distal end of the cutting tube may be configured to cut through a portion of the retention member 45, so that the resorbable anchor 40 can be detached from the device 10 and left in a patient.

Figure 8:
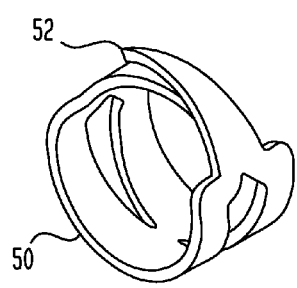
FIG. 8 is a perspective view of the clip of FIG. 7, shown in a closed condition.

Referring again to FIGS. 2 and 3, the device 10 may include a tissue securing component in the form of a clip 50 that is configured to be applied around a captured portion of the posterior leaflet 2 that has been partially drawn into the lumen of the outer tube 16. The clip 50 may be made of a shape memory metal, spring steel, or any other elastically deformable, biologically inert metal or polymer and may be biased to curl or contract into a substantially round or clamping condition (FIG. 8) when deployed from the outer tube 16. A prong 52 at each end of the clip 50 may be configured to become embedded in the leaflet tissue when the clip is deployed.

One or more clips 50 may be disposed in an open or expanded condition around the outer surface 19 of the outer tube 16 adjacent the open distal end 17 thereof. A deployment tube 54 may be slideably disposed with a tight clearance around the outer tube 16, such that the clip 50 will interfere with the an end surface 56 of the deployment tube as the deployment tube is moved toward the open distal end 17 of the outer tube. For example, the deployment tube 54 may be movable between a proximal position in which the end surface 56 is spaced apart from the open distal end 17 of the outer tube 16 and a distal position in which the end surface is adjacent the open distal end. The end surface 56 may be adapted to push the clip 50 off of the outer tube 16 when the deployment tube 54 is moved from the proximal position to the distal position.

To use the device 10 to gather heart valve leaflet tissue, the nosecone 30 may be assembled over the distal end 17 of the outer tube 16, such that the free edge 31 thereof is located proximally of the clip or clips 50 that have been assembled in an expanded condition around the outer tube. Next, the distal portion 14 of the catheter assembly 12 may be inserted into a patient, for example, through the apex of the heart into the left ventricle, so that the distal portion is near the mitral valve 1. The distal portion 14 of the catheter assembly 12 may be guided using three-dimensional echocardiography or another imaging technique to visualize the outer tube or other components of the catheter assembly.

With the device 10 positioned as described above, the user may grasp and pull the free end of the actuation member 35 (or may operate a button or other mechanism that performs this function) to remove the nosecone 30 from the distal end 17 of the outer tube 16. The actuation member 35 must be pulled in a proximal direction with enough force to overcome the friction between the peripheral portion 34 of the nosecone 30 and the deployment tube 54. If the nosecone 30 has one or more preformed slits 36 or tearable perforations 38, the pulling force may cause adjacent sections 34a, 34b, and 34c of the peripheral portion to separate from one another, thereby reducing the friction between the nosecone and the deployment tube that must be overcome to move the nosecone.

As the user pulls the free end of the actuation member 35 proximally, the nosecone 30 begins to move from the protective condition shown in FIG. 2 to the inverted condition shown in FIG. 3 in the lumen of the outer tube 16. Continued pulling on the free end of the actuation member 35 causes the entire nosecone 30 to enter the lumen of the outer tube 16 and to be pulled proximally therein until no portion of the nosecone overlies any portion of the clip or clips 50. The user may leave the nosecone 30 inside the lumen of the outer tube 16 or may continue to pull the actuation member 35 proximally until the nosecone reaches a proximal portion of the device 10 (not shown), where it may be removed from the device by the user.

After removal of the nosecone 30, the containment tube 20 may be deployed by sliding the distal portion 21 thereof beyond the distal end 17 of the outer tube 16. The deployed containment tube 20 may be guided such that its distal end 21 contacts the lower surface 9a of the posterior leaflet 2 in a target region thereof to be captured. For example, the target portion of the posterior leaflet 2 to be captured may be a loose edge of the leaflet below the coaption line 5.

Then, the needle 22 may be deployed by sliding the needle distally out of the containment tube 20, such that the tapered distal end 23 of the needle pierces the posterior leaflet 2 and extends therethrough to the upper surface 9b of the leaflet. The anchor 40 may then be deployed from the needle 22 by increasing the pressure within the needle using pressurized saline, for example. With the anchor 40 ejected, the needle 22 may be withdrawn from the posterior leaflet 2 and retracted into the containment tube 20, leaving the anchor adjacent the upper surface 9b of the leaflet and the retention member 45 extending through the opening in the leaflet created by the needle. The retention member 45 may then be pulled proximally by the user until the bottom surface 42 of the anchor 40 contacts the upper surface 9b of the leaflet.

The user may then slide the containment tube 20 proximally to the retracted position within the lumen of the outer tube 16, thereby drawing the anchor 40 proximally, and with it the posterior leaflet 2, until a portion 8 of the posterior leaflet is drawn into the open end of the outer tube.

The user may then push the deployment tube 54 distally until the end surface 56 thereof contacts the clip 50 and pushes it in a distal direction off of the distal end 17 of the outer tube 16. As the clip 50 is released from the outer tube 16, it will collapse to a substantially round or clamping condition according to its bias, and the two prongs 52 of the clip will become embedded in the captured tissue 8 of the posterior leaflet 2, thereby securing the tissue. If a plurality of clips 50 are disposed adjacent one another at the distal end 17 of the outer tube 16, additional clips can be deployed one at a time onto the posterior leaflet 2 by continuing to move the deployment tube 54 distally until all of the desired clips have been pushed off of the outer tube.

After the clip or clips 50 have been secured into the captured tissue 8 of the posterior leaflet 2 as described above, the retention member 45 may be detached from the anchor 40, for example, by pulling the retention member proximally until at least a portion of the retention member is torn from the anchor. The entire retention member 45 may be detached from the anchor 40, or the retention member may have a weakened portion near the attachment location with the anchor that is adapted tear when sufficient pulling force is applied by the user. Alternatively, at least a portion of the retention member 45 may be detached from the anchor 40 by cutting the retention member using a cutting mechanism, such as the cutting tube described above. The entire device may then be removed from the patient, and the anchor 40 that is left in the captured tissue of the posterior leaflet 2 may be resorbed over time.

As noted above, the actuation member 35 may be a shaft, tube, or rigid wire that has some structural rigidity when a compressive force is applied thereto, rather than simply a length of suture or flexible wire. In such case, instead of simply pulling the nosecone 30 into the lumen of the outer tube 16, a user may slide the actuation member distally, thereby pushing the nosecone off of the distal end 17 of the outer tube 16. Once the nosecone 30 has been removed from the outer tube 16, the user may pull the actuation member proximally until the nosecone enters the lumen of the outer tube 16. In such an embodiment, the nosecone 30 may be made of a shape memory material that is biased to collapse when pushed off of the outer tube 16 from the expanded protective condition shown in FIG. 2 to a smaller profile (e.g., a collapsed condition) that is able to fit within the lumen of the outer tube.

In the foregoing, particular structures have been described that are adapted to gather, secure, and repair heart valve leaflet tissue. The invention also contemplates the use of any alternative structures for such purposes, including structures having different lengths, shapes, and configurations.

Although the nosecone 30 is described in the context of a device having a tissue capture tool in the form of a needle 22 and a resorbable anchor 40 and having a tissue securing component in the form of a clip 50 that is configured to be deployed from around the outer surface 19 of the outer tube 16, the nosecone may be used with devices having other configurations of tissue capture tools and tissue securing components. Some suitable examples of such tissue capture tools and tissue securing components can be found in the copending and commonly owned U.S. Provisional Patent Application No. 61/590,557, filed Jan. 25, 2012.

Although the nosecone 30 has been described herein in the context of a device that can tighten the posterior or anterior leaflet of a mitral valve, such a nosecone can be used with any device used percutaneously in a patient. For example, the nosecone 30 or a smaller nosecone can be used with a device that can treat the leaflets of other heart valves, or with a device that can treat any other tissue of the body.

Although the invention herein has been described with reference to particular embodiments in which the catheter assembly is inserted into the patient through the apex of the heart (i.e., transapical insertion), it is to be understood that the invention contemplates embodiments in which the catheter assembly extends through a portion of the vasculature of the patient to reach the heart, for example, through a transfemoral or subclavian artery, or using a transseptal procedure. Any other percutaneous technique for accessing the interior of the heart may also be used. In such embodiments, some of the device components may have to be oriented in a different direction to that described herein. For example, the invention contemplates embodiments in which the distal portion of the catheter assembly approaches the mitral valve from the either the upstream side or the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for gathering tissue of a heart valve leaflet, the device comprising:
   an outer tube extending in an elongation direction and having an open distal end, the outer tube having an outer surface and a lumen extending therethrough, the lumen having a first cross-section;
   a capture tool movable in the outer tube between a contained position and a use position, the capture tool being operable to capture tissue of the heart valve leaflet and to draw the captured tissue into the outer tube in a gathered configuration;
   a tissue securing component disposed at the open distal end of the outer tube and adapted to be applied to the captured tissue to hold the captured tissue in the gathered configuration;
   a nosecone removably assembled over the open distal end of the outer tube in a protective condition, the nosecone having a central portion that extends across the open distal end of the outer tube and a peripheral portion surrounding the central portion and overlying the outer surface of the outer tube adjacent the open distal end; and a rigid actuation member joined to the central portion of the nosecone and extending into the lumen of the outer tube, wherein the nosecone is configured to move from the protective condition to a collapsed condition when the nosecone is pushed off of the distal end of the outer tube by distal movement of the actuation member relative to the outer tube, and wherein the nosecone is made of a shape memory material that is biased toward the collapsed condition, the nosecone in the collapsed condition having a second cross-section that is smaller than the first cross-section.

2. The device of claim 1, wherein the actuation member is joined to the nosecone substantially at the center of the central portion.

3. The device of claim 1, wherein the nosecone is made of a fabric.

4. The device of claim 1, wherein the nosecone is made of silicone.

5. The device of claim 1,
wherein the nosecone includes a slit extending from a free edge of the nosecone toward the central portion of the nosecone, the slit dividing the peripheral portion into a plurality of sections such that when the actuation member is pulled in the elongation direction, the plurality of sections separate from one another.

6. The device of claim 1, wherein the nosecone includes a line of perforations extending from a free edge of the nosecone toward the central portion of the nosecone, the line of perforations dividing the peripheral portion into a plurality of sections such that when the actuation member is pulled in the elongation direction, the perforations tear to separate the sections from one another.

7. The device of claim 1, wherein the tissue securing component is a clip.

8. The device of claim 7, wherein the clip is assembled in an expanded condition around the outer tube and is biased to contract to a clamping condition when deployed from the outer tube.

9. The device of claim 8, further comprising a deployment tube slidably disposed around the outer tube, the deployment tube movable between a proximal position in which an end surface thereof is spaced apart from the open distal end of the outer tube and a distal position in which the end surface is adjacent the open distal end, the end surface of the deployment tube being adapted to push the clip off of the outer tube when the deployment tube is moved from the proximal position to the distal position.

10. A transcatheter method of gathering tissue of a heart valve leaflet, the method comprising:
inserting an elongated catheter assembly to a position adjacent the heart valve leaflet, the catheter assembly including an outer tube extending in an elongation direction and having a lumen with a first cross-section, a capture tool movable in the outer tube between a contained position and a use position, a nosecone biased toward a collapsed shape and movable between a protective condition enclosing an open distal end of the outer tube and a deployed condition removed from the distal end of the outer tube, and an actuation member joined to a central portion of the nosecone;

moving the nosecone from the protective condition to the deployed condition to thereby expose the open distal end of the outer tube by pushing the actuation member in the elongation direction until the nosecone is pushed off of the distal end of the outer tube and takes the collapsed shape, the collapsed shape having a second cross-section that is smaller than the first cross-section;

moving the capture tool from the contained position to the use position;

capturing tissue of the heart valve leaflet with the capture tool;

retracting the capture tool from the use position toward the contained position to draw the captured tissue into the outer tube in a gathered configuration; and securing the captured tissue substantially in the gathered configuration.

11. The method of claim 10, wherein the step of moving the nosecone further includes pulling the actuation member in the elongation direction until the nosecone is pulled into the lumen of the outer tube.

12. The method of claim 10, wherein the nosecone is made of a shape memory material.

13. The method of claim 10, wherein the actuation member is rigid.

14. The method of claim 10, wherein the nosecone has a peripheral portion surrounding the central portion, and a slit extending from a free edge of the nosecone toward the central portion of the nosecone and dividing the peripheral portion into a plurality of sections, and the step of moving the nosecone includes separating the plurality of sections from one another.

15. The method of claim 10, wherein the nosecone has a peripheral portion surrounding the central portion, and a line of perforations extending from a free edge of the nosecone toward the central portion of the nosecone and dividing the peripheral portion into a plurality of sections, and the step of moving the nosecone includes separating the plurality of sections from one another along the line of perforations.

16. The method of claim 10, wherein the tissue securing component is a clip assembled in an expanded condition around the outer tube and biased to contact to a clamping condition, and the securing step includes deploying the clip from the outer tube, whereupon the clip contracts to the clamping condition around the captured tissue.

17. The method of claim 16, wherein the catheter assembly further includes a deployment tube slidably disposed around the outer tube, and the securing step includes moving the deployment tube from a proximal position in which an end surface thereof is spaced apart from the open distal end of the outer tube to a distal position in which the end surface is adjacent the open distal end, such that the deployment tube pushes the clip off of the outer tube.

* * * * *